United States Patent [19]

Berenson

[11] 3,947,583

[45] Mar. 30, 1976

[54] METHOD FOR CONTROLLING FUNGI UTILIZING PYRAZOLINIUM COMPOUNDS

[75] Inventor: Herman Berenson, Trenton, N.J.

[73] Assignee: American Cyanamid Company, Stamford, Conn.

[22] Filed: Jan. 13, 1975

[21] Appl. No.: 540,736

[52] U.S. Cl. ............................................. 424/273
[51] Int. Cl.² ........................................... A01N 9/22
[58] Field of Search ................ 424/273; 260/310 B

[56] References Cited
FOREIGN PATENTS OR APPLICATIONS 2,260,485   6/1973   Germany
1,315,825   5/1973   United Kingdom

*Primary Examiner*—Stanley J. Friedman
*Assistant Examiner*—Allen J. Robinson
*Attorney, Agent, or Firm*—Harry H. Kline

[57] ABSTRACT

There is provided a method for controlling plant pathogenic fungi utilizing an effective amount of 1,2-dialkyl-3,5-disubstituted and -3,4,5-trisubstituted pyrazolinium salts.

9 Claims, No Drawings

METHOD FOR CONTROLLING FUNGI UTILIZING PYRAZOLINIUM COMPOUNDS

The present invention relates to a method for controlling fungi with pyrazolinium salts represented by the formula:

(I) 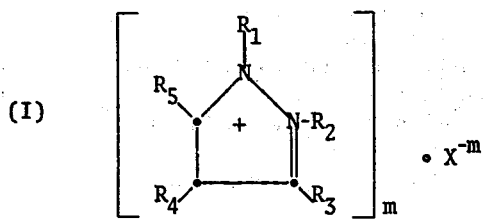 $\cdot X^{-m}$ wherein $R_1$ and $R_2$ each represent alkyl $C_1$–$C_4$; $R_4$ represents hydrogen or methyl; $R_3$ and $R_5$ each represent

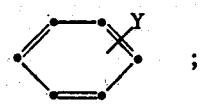

X represents an anion having a charge of from 1 to 3, $m$ is an integer from 1 to 3 and Y represents hydrogen, halogen, alkyl ($C_1$–$C_4$), or alkoxy ($C_1$–$C_4$).

Illustrative of the anions, represented by X, which are suitable for use in the present invention may be mentioned, for example, halides such as chloride, bromide or iodide; acetate; sulfate; hydrogen sulfate; methyl sulfate; benzene sulfonate; $C_1$–$C_3$ alkyl benzene sulfonate, such as p-toluene sulfonate; nitrate; phosphate; carbonate; perchlorate and tetrafluoroborate.

With regard to pyrazolinium salts of the present invention, it is to be understood that certain multivalent anions such as sulfate, phosphate, and the like may have associated with them a cation in addition to the pyrazolium cation, as for example, a proton or an alkali metal or alkaline earth metal. For simplicity, such anions are characterized as being unionized although they probably are in fact further ionized. Typical representations are: $NaSO_4^-$, $KPO_4^-$, $MgPO_4^-$, $HSO_4^-$, $NaHPO_4^-$, and the like.

As herein employed, term "halogen" is intended to mean chlorine, bromine, iodine and fluorine.

In general, the pyrazolinium compounds employed in the process of the invention can be prepared by several procedures. One procedure, hereinafter referred to as Procedure A, involves the condensation of an α,β-unsaturated ketone with an equimolar amount, and preferably an excess of from 1 to 2 mole equivalents of a 1,2-dialkylhydrazine salt. This reaction is preferably conducted in the presence of a protonic solvent such as a lower alcohol $C_1$–$C_4$ or acetic acid, and usually requires elevated temperatures of from about 50°C. to 150°C., and preferably 75°C. to 100°C., and an extended reaction period of from about 2 hours to 2 weeks. A 24- to 48-hours reflux period is frequently employed; however, a shorter reflux period can also be used. The pyrazolinium products can be isolated from said unreacted α,β-unsaturated ketone or chalcone by virtue of their water solubility. Isolation can be achieved by evaporation of the solvent from the reaction mixture, dissolution of the remaining residue in water, and extraction of impurities with ether. The appropriate salt of the pyrazolinium ion can next be obtained from the aqueous solution by evaporation of the water. The anion of the 1,2-dialkylhydrazine salt will be the anion of the pyrazolinium salt. Ion exchange chromatography may be used to exchange the anion of the pyrazolinium salt. The exchange may be affected by treating the initially formed salt with an ion exchange resin. Among the suitable ion exchange resins, one may mention a strong base organic anion exchanger, such as Dowex 1-x8. Illustrative exchangers employ quaternary ammonium salts. Where the resin is supplied as the salt of an anion other than that desired, it is pretreated with an aqueous solution of a salt of the desired anion. For example, if the resin is supplied as a quaternary ammonium chloride and it is desired to produce a pyrazolinium bromide, one would pretreat the resin with hydrobromic acid.

Other modifications of the anion in the pyrazolinium salt can also be affedted. For instance, a pyrazolinium chloride can be conveniently converted to the corresponding bromide, iodide or perchlorate by treatment with aqueous hydrogen bromide, aqueous sodium iodide or aqueous perchloric acid, respectively. Further, the methyl sulfate can be exchanged for other anions, such as $Cl^-$, $NO_3^-$ or $CH_3COO^-$, by adding to an aqueous solution of the methyl sulfate salt such salts as calcium chloride, calcium nitrate or calcium acetate either as a salt or as an aqueous solution. Insoluble calcium methyl sulfate precipitates and is removed by filtration. The desired pyrazolinium salt can be isolated as a solid from the aqueous medium by extraction with chloroform and then removal of the chloroform by evaporation.

The reaction of Procedure A may be graphically illustrated as follows:

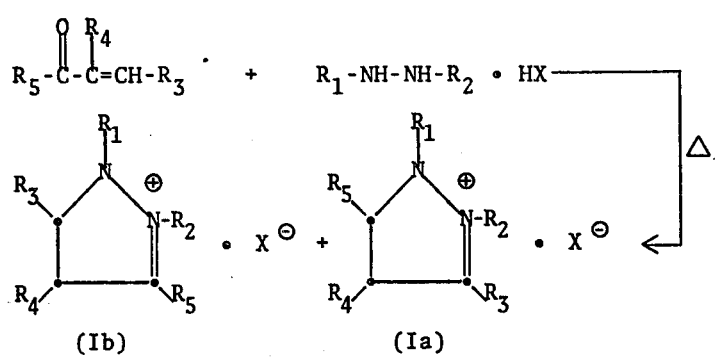

where $R_1$, $R_2$, $R_3$, $R_4$, $R_5$ and X are each as defined above. As shown, when $R_1$=$R_2$, Procedure A gives the predominant product as (Ib) involving reaction first at the carbonyl carbon center. Thus, this procedure can be used to prepare isomers (Ia) or (Ib) by selection of the appropriate starting chalcone.

Pyrazolinium compounds of the present invention depicted by formula (I) can also be prepared by reduction of the appropriate pyrazolium compound. This procedure is, hereinafter, referred to as procedure B, and involves treatment of a pyrazolium salt with a reducing agent such as lithium aluminum hydride or sodium borohydride. The reduction with sodium borohydride is generally conducted in the presence of a solvent such as alcohol. Other suitable solvents include $C_1$–$C_6$ saturated alcohols, isopropyl alcohol being preferred. This reaction is generally carried out at an elevated temperature between about 20°C. and 100°C. using equimolar amounts of the pyrazolium compound and the reducing agent. The reduction with lithium aluminum hydride is conducted in other solvents such as diethyl ether, dimethyl ether, methylethyl ether, tetrahydrofuran, in the temperature range of from 20°C. to 100°C.

After the reduction, the resulting 3-pyrazoline is protonated with an appropriate acid, HX, to give the pyrazolinium salt. This reaction is graphically illustrated as follows using sodium borohydride as a representative reducing agent:

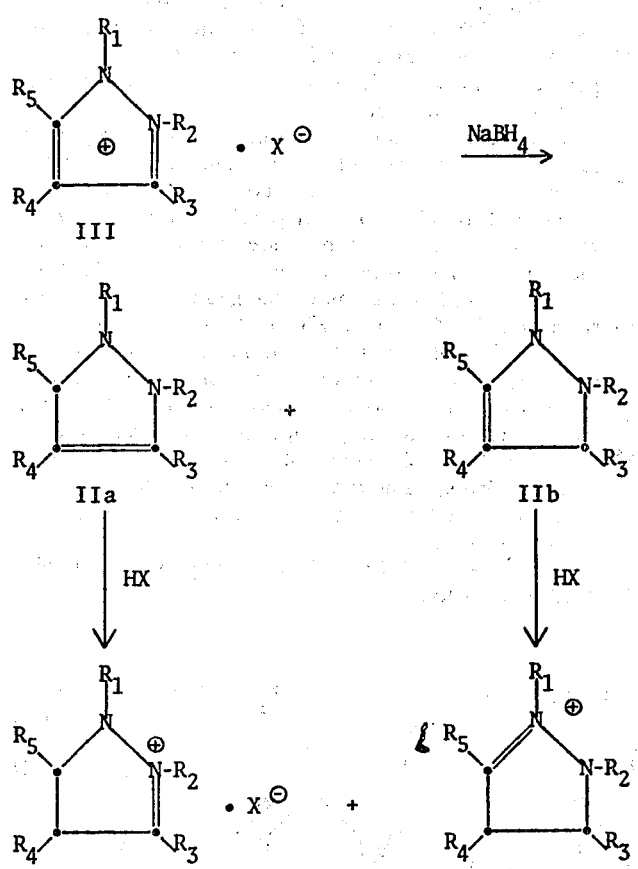

where $R_1$, $R_2$, $R_3$, $R_4$, $R_5$ and X are each as defined above. It will be recognized that IIa and IIb are tautomers forms of the same basic structure. Similarly the two pyrazolinium cations are tautomers. In any given reductive sequence as shown above, either or both of the tautomers pyrazoline and pyrazolinium salt may be obtained.

The 3-pyrazolines (IIa and IIb) can be isolated directly from the reduction, if desired, by avoiding protonation in the work-up procedure.

Illustrative of the compounds which can be prepared by one or both of the above procedures are:

1,2,4-Trimethyl-3,5-diphenyl-2-pyrazolinium iodide;

5-(m-Fluorophenyl)-1,2-dimethyl-3-phenyl-2-pyrazolinium bromide;

5-(o-Fluorophenyl)-1,2-dimethyl-3-phenyl-2-pyrazolinium methyl sulfate;

5-(p-Fluorophenyl)-1,2-dimethyl-3-phenyl-2-pyrazolinium hydrogen sulfate;

3-(p-Fluorophenyl)-1,2-dimethyl-5-phenyl-2-pyrazolinium perchlorate;

1,2-Dimethyl-3-o-totlyl-5-p-tolyl-2-pyrazolinium iodide;

1,2-Dimethyl-5-o-tolyl-3-p-tolyl-2-pyrazolinium methyl sulfate;

1,2-Dimethyl-3,5-di-m-tolyl-2-pyrazolinium methyl sulfate;

3-(p-Chlorophenyl)-1,2-dimethyl-5-phenyl-2-pyrazolinium benzene sulfonate;

1,2-Dimethyl-3,5-di-o-tolyl-2-pyrazolinium iodide;

5-Anisyl-1,2-dimethyl-3-phenyl-2-pyrazolinium perchlorate;

1,2-Dimethyl-3-phenyl-5-m-tolyl-2-pyrazolinium iodide, and 1,2-Dimethyl-5-phenyl-3-m-tolyl-2-pyrazolinium iodide.

The compounds of the present invention, as represented by formula (I) above, and derivatives thereof, are highly effective as foliar fungicidal agents. They are particularly effective when applied to the foliage of plants at a rate between about 0.56 kg and 11.2 kg per hectare, and preferably from 0.56 kg to 4.48 kg per hectare.

For application of the formula (I) pyrazolinium salts to the foliage of plants, the salts are generally formulated as fungicidal compositions by admixing a suitable fungicidal adjuvant with a fungicidally effective amount of the salt. Suitable adjuvants include one or more conventiona solid or liquid carriers, diluents and formulation aids, particularly surfactants.

The active compounds may be formulated as dusts, dust concentrates, wettable powders or water-miscible concentrates; however, the water-miscible concentrates are especially advantageous.

Dusts are readily prepared by grinding together about 1% to 25% by weight of the active agent with from about 99% to 75% by weight of a solid diluent such as kaolin, attapulgite, diatomaceous earth, or the like. Dust concentrates are prepared in similar fashion excepting that about 25% to 95% by weight of the active agent is ground with about 75% to 5% by weight of the diluent.

Wettable powders are prepared in the same manner as the dust concentrates excepting that about 1% to 5% by weight of a dispersing agent such as sodium lignosulfonate, or the sodium salt of condensed naphthalene sulfonic acid is blended with the mixture and about 1% to 5% of a surfactant, such as a polyoxyethylated vegetable oil or an alkyl phenoxy polyoxyethylene ethanol, is also blended with the formulation. In practice, the powder is mixed with water and applied to the plant foilage as an aqueous spray.

Water-miscible concentrates are prepared by dissolving from 15% to 70% of the compound in 85% to 30% of a water-miscible solvent, such as water itself or another polar water-miscible solvent, such as 2-methoxy ethanol, methanol, propylene glycol, diethylene glycol, diethylene glycol monoethyl ether, formamide and methylformamide. Application of the material is made by adding a predetermined quantity of the water-miscible concentrate to a spray tank and applying the concentrate as such or in combination with an additional quantity of water or other polar solvent as a liquid spray.

The invention is further illustrated by the examples set forth below. These examples are provided only by way of illustration and are not intended to be limiting on the invention.

EXAMPLE 1

Preparation of 1,2-Dimethyl-3,5-diphenyl-2-pyrazolinium iodide, Utilizing "Procedure A" above.

An absolute ethanol solution of sym-dimethyl-hydrazine dihydriodide [sym-dimethylhydrazine dihydriodide is prepared from sym-dimethylhydrazine dihydrochloride (13.3 g, 0.1 mole) in ethanol by refluxing with an excess of potassium iodide (33.2 g, 0.2 mole) for 3 hours], is added to an absolute ethanol suspension of chalcone (15.6 g). The reaction mixture is heated to reflux with constant stirring and maintained there for 18 hours. After allowing the reaction mixture to cool to room temperature, the solvent is removed by evaporation, and the resulting mixture stirred with an aqueous potassium iodide solution.

The resulting solid is filtered and dried to give 5.95 g (21%), melting point 175°C. to 176°C. of 1,2-dimethyl-3,5-diphenyl-2-pyrazolinium iodide.

EXAMPLE 2

Preparation of 1,2-Dimethyl-3,5-diphenyl-2-pyrazolinium perchlorate, Utilizing "Procedure B" above.

Sodium borohydride (1.95 g) is added to a partial solution of 1,2-dimethyl-3,5-diphenylpyrazolium methyl sulfate (17.75 g) in isopropanol (700 ml). The reaction mixture is heated to reflux with stirring and maintained at reflux for 6 hours. After allowing the reaction mixture to cool to room temperature, it is stirred for 12 hours. The solvent is then removed by evaporation, and the resulting mixture slurried in water and extracted with benzene Evaporation of the organic layer yields an oil which is slurried in water and treated with perchloric acid. The aqueous solution is decanted away from the resulting tacky solid which is then treated with 95% ethanol. The resulting white solid is filtered and dried to yield 8.5 g (51%), melting point 183°C to 185°C of 1,2-dimethyl-3,5-diphenyl-2-pyrazolinium perchlorate.

EXAMPLE 3

Following Procedure A, as described in Example 1 above, and employing the appropriate $\alpha,\beta$-unsaturated ketones and symmetrical dialkyl hydrazine salt, there is obtained each of the following compounds set forth:

3,5-Diphenyl-1,2,4-trimethyl-2-pyrazolinium iodide; mp 175°C–176°C (dec.)

1,2-Dimethyl-3,5-bis-o-tolyl-2-pyrazolinium iodide; mp 166°C–168°C (dec.)

1,2-Dimethyl-3,5-bis-m-tolyl-2-pyrazolinium iodide; mp 94°C–96°C 1,2-Dimethyl-3-o-tolyl-5-p-tolyl-2-pyrazolinium iodide; mp 146°C–149°C 1,2-Dimethyl-5-o-tolyl-3-p-tolyl-2-pyrazolinium iodide; mp 175°C–176°C 1,2-Dimethyl-3-phenyl-5-m-tolyl-2-pyrazolinium iodide; mp 148°C–150°C 1,2-Dimethyl-5-phenyl-3-m-tolyl-2-pyrazolinium iodode; mp 143°C–145°C 1,2-Dimethyl-m-methoxyphenyl-5-phenyl-2-pyrazolinium perchlorate; mp 120°C–126°C 1,2-Dimethyl-3-p-fluorophenyl-5-phenyl-2-pyrazolinium iodide; mp 165°C–167°C 1,2-Dimethyl-5-p-fluorophenyl-3-phenyl-2-pyrazolinium iodide; mp 137°C–139°C 1,2-Diemthyl-5-m-fluorophenyl-3-phenyl-2-pyrazolinium perchlorate; mp 148°C–149°C (dec.)

1,2-Dimethyl-5-o-fluorophenyl-3-phenyl-2-pyrazolinium perchlorate; mp 148°C–149°C (dec.)

1,2-Dimethyl-5-p-fluorophenyl-3-phenyl-2-pyrazolinium iodide; mp 137°C–139°C (dec.)

1,2-Dimethyl-3-p-chlorophenyl-5-phenyl-2-pyrazolinium perchlorate; mp 161°C–166°C

EXAMPLE 4

To determine the effectiveness of pyrazolinium salts as fungicidal agents a variety of pathogenic fungi, host plants, and pyrazolinium salts are used in the following tests. Pathogens, host plants, the method of testing and the rating system used are reported below along with the data obtained.

Pathogens:
*Piricularia oryzae* Cavara, the rice blast pathogen.
*Venturia inaequalis* (Cke.) Wint. which causes apple scab.
*Erysiphe cichoracearum* DC, the cause of powdery mildew on cucurbits.
*Podosphaera leucotricha* (E. & E.) Salm., the cause of powdery mildew of apples and pears.
*Erysiphe graminis* f. sp. *tritci* the cause of powdery mildew on wheat.
*Phytophthora infestans* (Mont.) Dby. the late blight fungus of tomato and potato.
*Erysiphe graminis* f. sp. *hordei* the cause of powdery mildew on barley.

Host Plants:
Rice (*Oryza sative*) (Cv. Nato)
Cucumber (*Cucumis sativus*) (Cv. Marketer)
Apple (*Malus sylvestris*) (Seedling)
Wheat (*Triticum aestivum* Cv. Bonanza)
Tomato (*Lycopersicon esculentum*) (Cv. Bonny Best)
Barley (*Hordeum vulgare* L. ) (Cv. Larker)

Plants are individually grown in 5.08 cm peat squares and assembled in 7.62 cm × 25.4 cm pressed fiber flats the week prior to spraying. With exception of rice, barley and wheat, a single specimen of each species is used. A separate container is used for those plants in the mildew evaluation. The complete test system is shown below.

| Series 1 | | Series 2 | |
|---|---|---|---|
| Rice: | Rice Blast | Apple: | Powdery Mildew |
| Apple: | Apple Scab | Cucumber: | Powdery Mildew |
| Tomato: | Tomato late blight | Wheat: | Powdery Mildew |
| | | Barley: | Powdery Mildew |

Spray solutions are prepared at a final concentration of 100 or 500 ppm pyrazolinium (salt or cation) in 50 ml of 50% aqueous acetone. In all cases, acetone is added first to solubilize the compound and solutions made to final volume with deionized water.

Two flats, with plants for each treatment, one each from Series 1 and 2 (see above), are sprayed simultaneously on a turntable with 50 ml of the test solution. Spray is provided by 2 fixed Spraying System Co. nozzles mounted to deliver vertical and horizontal solid cone spray patterns. Immediately thereafter, all plants, are returned to the greenhouse to permit the deposit to dry.

After the plants have dried, Series 1 and 2 are separately inoculated. Plants in Series 1 are inoculated with conidial suspensions of the respective pathogens using a DeVilbiss paint sprayer operated 4–6 psig and immediately transferred to a controlled temperature/humidity cabinet (ambient temperature rh~95%). Plants in Series 2 are dusted with respective powdery mildew conidia and then removed to the greenhouse, to await disease development. Plants in Series 1 are held 4 days in the cabinet then transferred to the greenhouse to await disease expression.

All plants are rated for disease severity on a scale of 1–7 (clean-kill), as described below:

| Rating | Description |
|---|---|
| 1 | Nil |
| 2 | Trace disease |
| 3 | Slight disease |
| 4 | Moderate disease |
| 5 | Heavy disease |
| 6 | Severe disease |
| 7 | Kill |

Data obtained are reported in Tables I and II below. Ratings reflect only levels where effective control was observed and are mean ratings for all tests carried out with any given compound.

Table I

| | | (Series 1) Foliar Fungicidal Activity | | | | | |
|---|---|---|---|---|---|---|---|
| | | Rice Blast | | Tomato Late Blight | | Apple Scab | |
| Compound | ppm → | 500 | 100 | 500 | 100 | 500 | 100 |
| 1,2-Dimethyl-3,5-diphenyl-2-pyrazolinium iodide | | 3.5 | | | | | |
| 1,2-Dimethyl-3-o-tolyl-5-p-tolyl-2-pyrazolinium iodide | | 4.0 | | | | | |
| 1,2-Dimethyl-5-m-fluorophenyl-3-phenyl-2-pyrazolinium iodide | | 4.0 | | | | | |
| 1,2-Dimethyl-3-m-methoxyphenyl-5-phenyl-2-pyrazolinium perchlorate | | | | | | 4.0 | |
| 1,2-Dimethyl-3,5-di-m-tolyl-2-pyrazolinium iodide | | | | | | 2.5 | |
| 1,2-Dimethyl-3-p-chlorophenyl-5-phenyl-2-pyrazolinium perchlorate | | | | 4.0 | | 1.0 | |
| 1,2-Dimethyl-5-o-fluorophenyl-3-phenyl-2-pyrazolinium perchlorate | | | | | | 4.0 | |
| 3,5-Diphenyl-1,2,4-Trimethyl-2-pyrazolinium iodide | | 4.0 | | | | | |
| 1,2-Dimethyl-3-p-fluorophenyl-5-phenyl-2-pyrazolinium iodide | | | | | | 3.6 | |
| 1,2-Dimethyl-5-o-tolyl-3-p-tolyl-2-pyrazolinium iodide | | 4.0 | | | | | |
| 1,2-Dimethyl-3,5-diphenyl-2-pyrazolinium perchlorate | | 4.0 | | | | 3.0 | 3.0 |
| No-Treatment Controls, Infected | | −5.6 | — | −5.25 | — | −6.0 | — |

Table II

| Compound ppm→ | (Series 2) Foliar Fungicidal Activity | | | | | | | |
| --- | --- | --- | --- | --- | --- | --- | --- | --- |
| | Cuc. Powdery Mildew | | Wheat Powdery Mildew | | Apple Powdery Mildew | | Barley Powdery Mildew | |
| | 500 | 100 | 500 | 100 | 500 | 100 | 500 | 100 |
| 1,2-Dimethyl-3,5-diphenyl-2-pyrazolinium iodide | | | 1.25 | 3.0 | 2.6 | | | |
| 1,2-Dimethyl-3-o-tolyl-5-p-tolyl-2-pyrazolinium iodide | | | 1.0 | | | | | |
| 1,2-Dimethyl-5-m-fluorophenyl-3-phenyl-2-pyrazolinium iodide | | | 1.0 | 1.0 | | | | |
| 1,2-Dimethyl-3,5-di-o-tolyl-2-pyrazolinium iodide | | | 2.0 | 2.0 | | 3.0 | | |
| 1,2-Dimethyl-5-p-fluorophenyl-3-phenyl-2-pyrazolinium iodide | | | 2.0 | | | | | |
| 1,2-Dimethyl-3-m-methoxyphenyl-5-phenyl-2-pyrazolinium perchlorate | | | 3.0 | 3.0 | | | | |
| 1,2-Dimethyl-3,5-di-m-tolyl-2-pyrazolinium iodide | | | 1.0 | 2.0 | | 3.0 | 1.0 | 4.0 |
| 1,2-Dimethyl-3-phenyl-5-m-tolyl-2-pyrazolinium iodide | 3.0 | | 1.0 | 1.0 | 2.0 | | | |
| 1,2-Dimethyl-5-phenyl-3-m-tolyl-2-pyrazolinium iodide | | | 1.0 | 2.0 | | 2.0 | | |
| 1,2-Dimethyl-5-o-fluorophenyl-3-phenyl-2-pyrazolinium perchlorate | | | 3.0 | | | | | |
| 3,5-Diphenyl-1,2,4-Trimethyl-2-pyrazolinium iodide | | 3.0 | 2.0 | 3.0 | | | | |
| 1,2-Dimethyl-3-p-fluorophenyl-5-phenyl-2-pyrazolinium iodide | | | 2.5 | | | | | |
| 1,2-Dimethyl-5-o-tolyl-3-p-tolyl-2-pyrazolinium iodide | | | 2.0 | | | | | |
| 1,2-Dimethyl-3,5-diphenyl-2-pyrazolinium perchlorate | | | 1.5 | 2.0 | 3.0 | | | |
| No Treatment Controls Infected | −6.0 | — | −6.0 | — | −5.6 | — | | |

I claim:

1. A method for the control of plant pathogenic fungi comprising: contacting said fungi with a fungicidally effective amount of a compound having the formula:

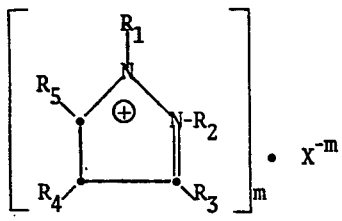

wherein $R_1$ and $R_2$ each represent alkyl $C_1-C_4$; $R_4$ represents hydrogen or methyl and; $R_3$ and $R_5$ each represent

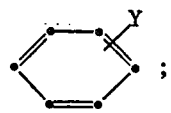

X represents an anion having a charge of from 1 to 3; $m$ is an integer from 1 to 3 and Y represents a member selected from the group consisting of hydrogen, halogen, alkyl $C_1-C_4$ and alkoxy $C_1-C_4$.

2. The method according to claim 1, wherein $R_1$ and $R_2$ are each methyl; $R_4$ represents hydrogen or methyl.

3. The method according to claim 1, wherein said compound is applied in an amount sufficient to provide from 0.56 kg to 11.2 kg per hectare.

4. The method according to claim 1, wherein $R_1$ and $R_2$ are each methyl; $R_4$ represents hydrogen or methyl; $R_3$ and $R_5$ each represent a member selected from the group consisting of phenyl, monohalophenyl, monomethylphenyl and monoalkoxy ($C_1-C_3$) phenyl; X is an anion having a single charge; and $m$ is 1.

5. The method according to claim 1, wherein said compound is applied in an amount sufficient to provide about 0.56 kg to 4.48 kg per hectare according to 6. The method according to claim 1, wherein said compound is applied at about 100 ppm to 5000 ppm.

7. The method according to claim 1, wherein $R_1$ and $R_2$ are each methyl; $R_4$ represents hydrogen; or methyl and; $R_3$ and $R_5$ each represent

X represents an anion having a charge of from 1 to 3; $m$ is an integer selected from 1, 2 and 3; and Y represents a member selected from the group consisting of hydrogen, halogen, alkyl $C_1-C_4$ and alkoxy $C_1-c_4$.

8. The method according to claim 1, wherein said compound is: 1,2-dimethyl-3,5-di-m-tolyl-2-pyrazolium iodide.

9. The method according to claim 1 wherein said compound is; 1,2-dimethyl-3,5-diphenyl-2-pyrazolinium perchlorate.

* * * * *